United States Patent
Goto

(10) Patent No.: US 11,478,203 B2
(45) Date of Patent: Oct. 25, 2022

(54) X-RAY COMPUTED TOMOGRAPHY APPARATUS AND IMAGING CONDITION MANAGEMENT APPARATUS

(71) Applicant: Canon Medical Systems Corporation, Otawara (JP)

(72) Inventor: Takahiro Goto, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 66 days.

(21) Appl. No.: 16/392,076

(22) Filed: Apr. 23, 2019

(65) Prior Publication Data

US 2019/0336089 A1 Nov. 7, 2019

(30) Foreign Application Priority Data

May 1, 2018 (JP) .............................. JP2018-088123

(51) Int. Cl.
*A61B 6/00* (2006.01)
*A61B 6/03* (2006.01)
*G01T 7/12* (2006.01)

(52) U.S. Cl.
CPC .............. *A61B 6/405* (2013.01); *A61B 6/032* (2013.01); *A61B 6/46* (2013.01); *A61B 6/542* (2013.01); *G01T 7/125* (2013.01)

(58) Field of Classification Search
CPC ......... A61B 6/405; A61B 6/032; A61B 6/542; A61B 6/46; A61B 6/5258; A61B 6/586; G01T 7/125; G01T 1/00
See application file for complete search history.

(56) References Cited

U.S. PATENT DOCUMENTS

| | | | | |
|---|---|---|---|---|
| 8,031,831 B2* | 10/2011 | Zou | ........................ | A61B 6/032 378/16 |
| 2003/0156679 A1* | 8/2003 | Mori | .................... | G01N 23/046 378/4 |
| 2007/0258896 A1* | 11/2007 | Nachaliel | ............... | A61B 6/488 424/9.1 |
| 2011/0311022 A1* | 12/2011 | Kappler | .................. | G01T 1/247 250/336.1 |

(Continued)

FOREIGN PATENT DOCUMENTS

| | | |
|---|---|---|
| JP | 2009-279289 | 12/2009 |
| JP | 2010-22869 | 2/2010 |

(Continued)

OTHER PUBLICATIONS

Japanese Office Action dated Mar. 8, 2022, issued in Japanese Patent Application No. 2018-088123.

(Continued)

*Primary Examiner* — Christine S. Kim
(74) *Attorney, Agent, or Firm* — Oblon, McClelland, Maier & Neustadt, L.L.P.

(57) ABSTRACT

According to one embodiment, an X-ray computed tomography apparatus includes an X-ray tube, a detector, and processing circuitry. The X-ray tube emits X-rays. The detector detects X-rays that have been emitted from the X-ray tube and have passed through the subject. The processing circuitry sets an imaging condition. The processing circuitry evaluates the imaging condition based on information on a lower limit range of a count value of the detected X-rays that may cause image degradation.

17 Claims, 4 Drawing Sheets

(56) References Cited

U.S. PATENT DOCUMENTS

| | | | |
|---|---|---|---|
| 2014/0098933 A1* | 4/2014 | Profio | A61B 6/465 378/19 |
| 2016/0317102 A1* | 11/2016 | Ishii | A61B 6/5205 |
| 2018/0088061 A1* | 3/2018 | Nakanishi | G01N 23/046 |

FOREIGN PATENT DOCUMENTS

| JP | 2010-193940 A | 9/2010 |
|---|---|---|
| JP | 2013-158630 A | 8/2013 |
| JP | 2007-152110 A | 9/2013 |
| JP | 2017-074299 A | 4/2017 |

OTHER PUBLICATIONS

Japanese Office Action dated Jul. 5, 2022, issued in Japanese Patent Application No. 2018-088123.

* cited by examiner

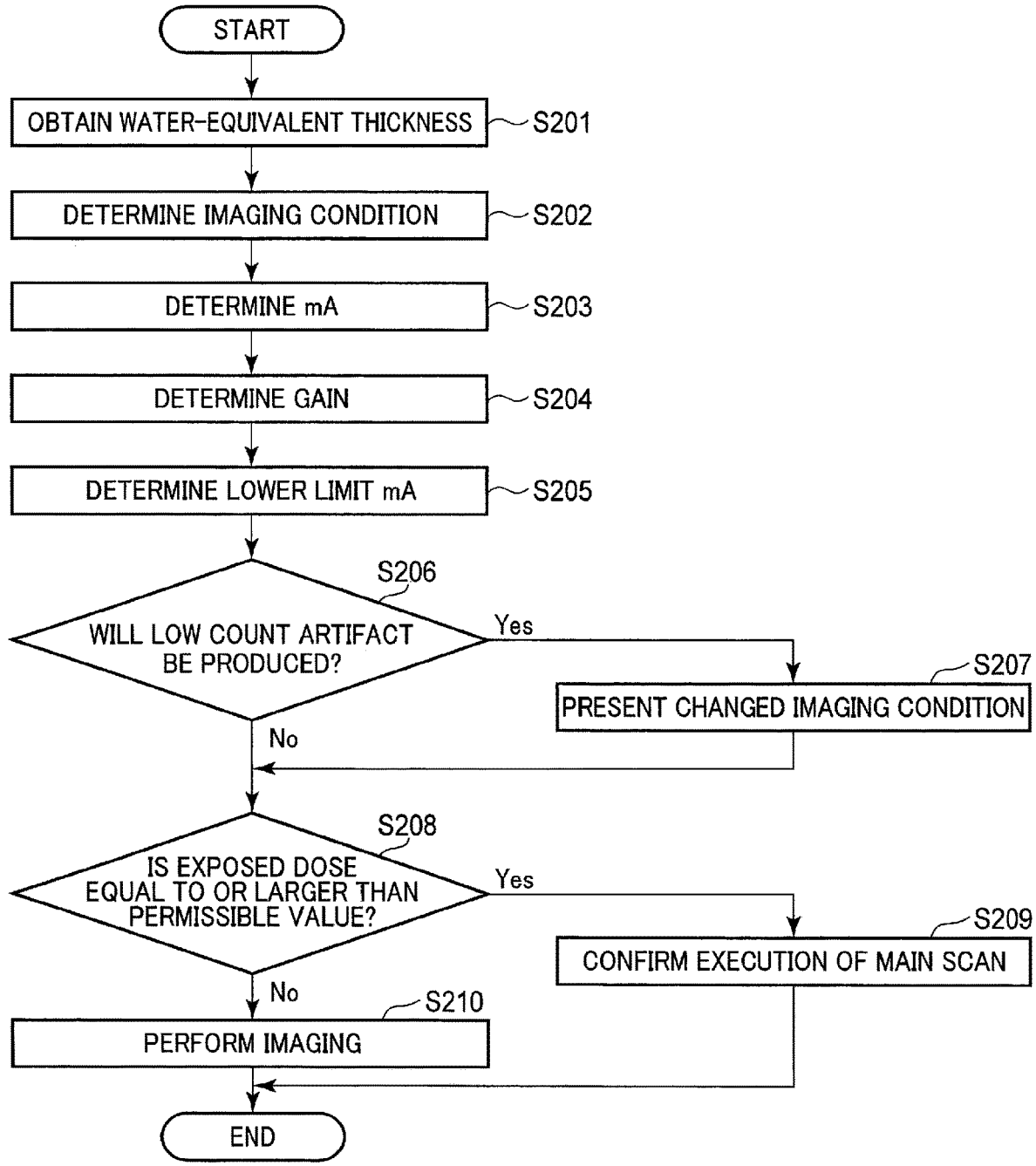
F I G. 2

| WATER-EQUIVALENT THICKNESS | RADIATION QUALITY PARAMETER | | ACQUISITION MODE | | . . . | COUNT VALUE LOWER LIMIT RANGE |
|---|---|---|---|---|---|---|
| | kv | WEDGE FILTER | ELEMENT SIZE | SITE | | |
| $a_1$ | $b_1$ | $c_1$ | $d_1$ | : | . . . | $0 \sim f_1$ |
| | | $c_2$ | | | | |
| | | : | $d_2$ | | | |
| | $b_2$ | $c_{10}$ | : | : | . . . | $0 \sim f_2$ |
| | | $c_{11}$ | | | | |
| | | : | | | | |
| | | | : | | | : |

X-RAY COMPUTED TOMOGRAPHY APPARATUS AND IMAGING CONDITION MANAGEMENT APPARATUS

CROSS-REFERENCE TO RELATED APPLICATIONS

This application is based upon and claims the benefit of priority from the prior Japanese Patent Application No. 2018-088123, filed May 1, 2018, the entire contents of which are incorporated herein by reference.

FIELD

Embodiments described herein relate generally to an X-ray computed tomography apparatus and an imaging condition management apparatus.

BACKGROUND

For determination of the imaging condition for X-ray imaging, a technique of tube current (mA) induction or tube voltage (kV) induction using auto exposure control (AEC) according to the subject body thickness is known. Image quality designated by the operator can basically be obtained by using the technique of mA induction or kV induction.

However, imaging with a low dose is now mainstream, and the imaging condition depends on the exposed dose. For example, although the subject size is large, imaging may be performed on the subject under the imaging condition similar to that for a normal-sized subject. In this case, the X-ray count value falls below a lower limit value, and a so-called low-count artifact is produced.

Under the existing AEC, an artifact (high-count artifact) produced when the X-ray count value exceeds an upper limit value is considered, but the low-count artifact is not considered. Therefore, the tube current is lowered as designated by the operator, and imaging is enabled even in the condition that causes a low-count artifact.

BRIEF DESCRIPTION OF THE DRAWINGS

FIG. 2 is a flowchart showing an operation of the X-ray computed tomography apparatus according to the present embodiment.

DETAILED DESCRIPTION

Figure 1:
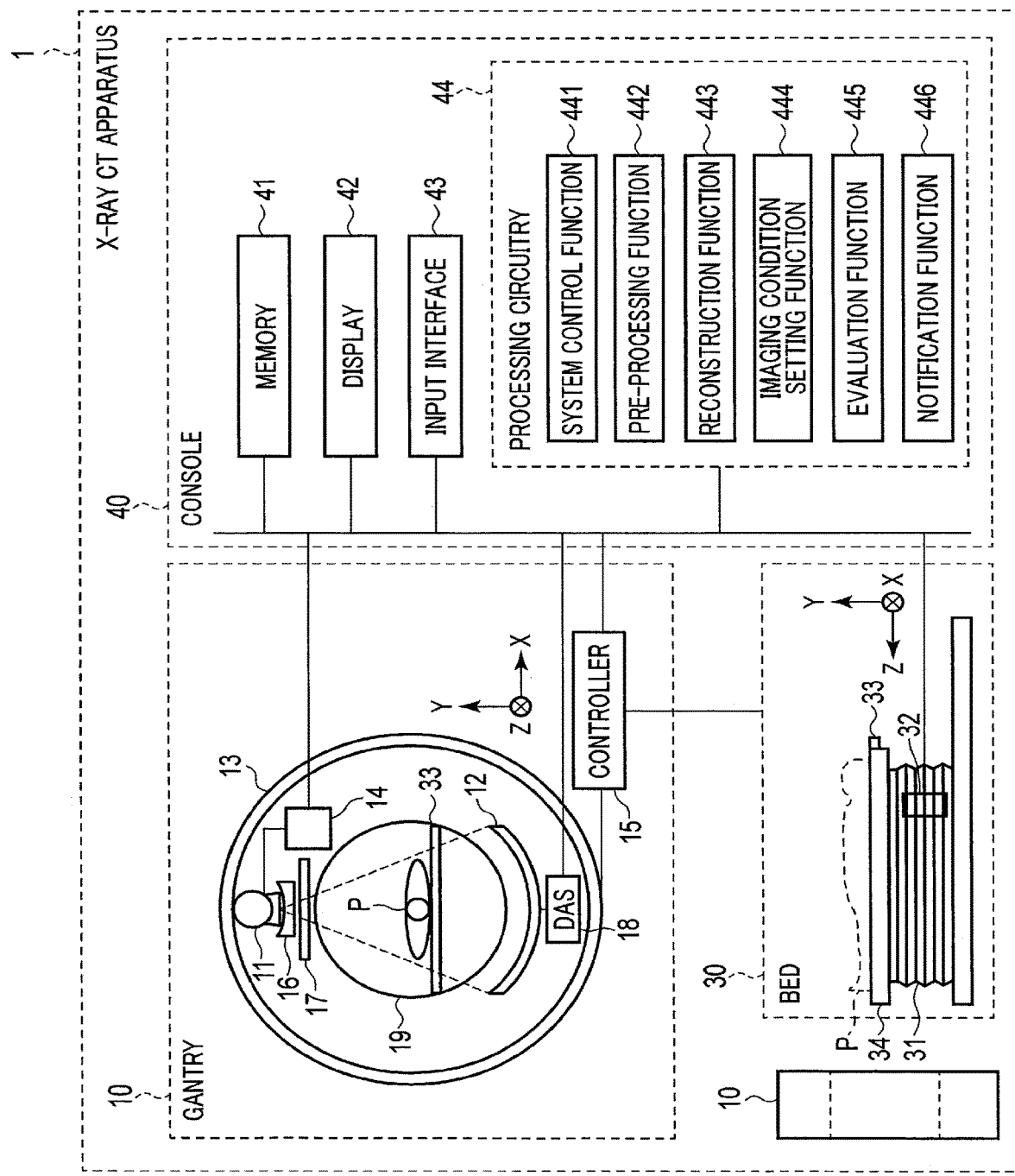
FIG. 1 is a block diagram showing a configuration of an X-ray computed tomography apparatus according to the present embodiment.

In general, according to one embodiment, an X-ray computed tomography apparatus includes an X-ray tube, a detector, and processing circuitry. The X-ray tube emits X-rays. The detector detects X-rays that have been emitted from the X-ray tube and have passed through the subject. The processing circuitry sets an imaging condition. The processing circuitry evaluates the imaging condition based on information on a lower limit range of a count value of the detected X-rays that may cause image degradation.

In the following description, an X-ray computed tomography (CT) apparatus and an imaging condition management apparatus according to the present embodiment will be described with reference to the drawings. In the following embodiments, elements assigned with the same reference numerals perform the same operations, and redundant descriptions will be omitted as appropriate.

Hereinafter, one embodiment will be described with reference to the drawings.

FIG. 1 is a block diagram showing a configuration of an X-ray CT apparatus according to one embodiment. The X-ray CT apparatus 1 shown in FIG. 1 includes a gantry 10, a bed 30, and a console 40. In the present embodiment, the rotation axis of a rotation frame 13 in the non-tilted state, or the longitudinal direction of a table top 33 of the bed 30, is defined as a "Z-axis direction"; the axial direction orthogonal to the Z-axis direction and horizontal to the floor is defined as an "X-axis direction"; and the axial direction orthogonal to the Z-axis direction and vertical to the floor is defined as a "Y-axis direction".

For example, the gantry 10 and the bed 30 are installed in a CT examination room, and the console 40 is installed in a control room adjacent to the CT examination room. The console 40 is not necessarily installed in the control room. For example, the console 40 may be installed together with the gantry 10 and the bed 30 in the same room. In any case, the gantry 10, the bed 30, and the console 40 are communicably connected to one another by wire or radio.

The gantry 10 is a scanner which has a configuration for performing X-ray CT imaging on a subject P. The gantry 10 includes an X-ray tube 11, an X-ray detector 12, rotation frame 13, an X-ray high voltage device 14, a controller 15, a wedge filter 16, a collimator 17, and a data acquisition system (DAS) 18.

The X-ray tube 11 is a vacuum tube that emits thermal electrons from the cathode (filament) to the anode (target) in response to application of a high voltage and supply of a filament current from the X-ray high voltage device 14. X-rays are generated by the thermal electrons colliding with the target. The X-rays generated in the X-ray tube 11 are, for example, formed into a cone-beam shape by the collimator 17, and applied to the subject P.

The X-ray detector 12 detects X-rays that have been emitted by the X-ray tube 11 and have passed through the subject P, and outputs an electrical signal corresponding to the X-ray dose to the DAS 18. The X-ray detector 12 includes a plurality of X-ray detection element lines, each including a plurality of X-ray detection elements aligned in a channel direction along an arc having a center at the focus of the X-ray tube 11, for example. The X-ray detector 12 has an array structure in which a plurality of X-ray detection element lines, each including a plurality of X-ray detection elements aligned in the channel direction, are aligned in a slice direction (row direction).

Specifically, the X-ray detector 12 is, for example, an indirect conversion type detector including a grid, a scintillator array, and an optical sensor array.

The scintillator array includes a plurality of scintillators. The scintillator includes a scintillator crystal that outputs light of a photon quantity corresponding to the incident X-ray dose.

The grid is arranged on the surface of the scintillator array on the X-ray incident side, and includes an X-ray shielding plate having the function of absorbing scattered X-rays.

The optical sensor array has the function of amplifying and converting light received from the scintillator into an electrical signal, and includes an optical sensor, such as a photomultiplier (PMT). The X-ray detector 12 may be a direct conversion type detector including a semiconductor element that converts incident X-rays into an electrical signal.

The rotation frame 13 supports an X-ray generator (11 and 16) and the X-ray detector 12 rotatably around a rotation axis. Specifically, the rotation frame 13 is an annular frame that supports the X-ray tube 11 and the X-ray detector 12 in such a manner that the X-ray tube 11 faces the X-ray detector 12, and rotates the X-ray tube 11 and the X-ray detector 12 under control of a controller 15 to be described later. The rotation frame 13 is rotatably supported by a stationary frame (not shown) made of a metal such as aluminum. Specifically, the rotation frame 13 is connected to an edge portion of the stationary frame via a bearing. The rotation frame 13 rotates around the rotation axis Z at a predetermined angular velocity while receiving power from a driver of the controller 15.

In addition to the X-ray tube 11 and the X-ray detector 12, the rotation frame 13 includes and supports the X-ray high voltage device 14 and the DAS 18. Such a rotation frame 13 is housed in an approximately-cylindrical case with a bore 19 constituting an imaging space. The bore approximately corresponds to the FOV. The central axis of the bore corresponds to the rotation axis Z of the rotation frame 13. Detection data generated by the DAS 18 is transmitted, for example, from a transmitter including a light-emitting diode (LED) to a receiver (not shown) including a photodiode and arranged on a non-rotating portion (such as the stationary frame) of the gantry by optical communication, and then transferred to the console 40. The method of transmitting detection data from the rotation frame to the non-rotating portion of the gantry is not limited to the above-described optical communication, and may be any scheme as long as the transmission is non-contact type data transmission.

The X-ray high voltage device 14 includes: a high voltage generator including electrical circuitry such as a transformer, a rectifier, etc. and having the function of generating a high voltage to be applied to the X-ray tube 11 and a filament current to be supplied to the X-ray tube 11; and an X-ray controller configured to control an output voltage in accordance with the X-rays emitted by the X-ray tube 11. The high voltage generator may be of a transformer type, or an inverter type. The X-ray high voltage device 14 may be provided in the rotation frame 13 to be described later, or in the stationary frame (not shown) of the gantry 10.

The controller 15 includes processing circuitry including a central processing unit (CPU), etc., and a driver such as a motor or an actuator, etc. The processing circuitry includes, as hardware resources, a processor, such as a CPU or a micro processing unit (MPU), and a memory, such as a read only memory (ROM) or a random access memory (RAM). The controller 15 may be realized by an application specific integrated circuit (ASIC), a field programmable gate array (FPGA), or another complex programmable logic device (CPLD) or simple programmable logic device (SPLD). The controller 15 controls the X-ray high voltage device 14 and the DAS 18, etc. in accordance with instructions from the console 40. The processor implements the above control by reading and executing a program stored in the memory.

The controller 15 also has the function of performing operation control of the gantry 10 and the bed 30 in response to an input signal from an input interface attached to the console 40 or the gantry 10. For example, the controller 15 performs control to rotate the rotation frame 13, control to tilt the gantry 10, or control to operate the bed 30 and the table top 33 in response to an input signal. The control to tilt the gantry 10 is implemented by the controller 15 rotating the rotation frame 13 around an axis parallel to the X-axis direction based on tilt angle information input through the input interface attached to the gantry 10. The controller 15 may be provided either in the gantry 10 or in the console 40. The controller 15 may be configured by directly integrating a program in the circuitry of the processor, instead of storing a program in the memory. In this case, the processor implements the above-described control by reading and executing the program integrated in the circuitry.

The wedge filter 16 is a filter for adjusting the dose of X-rays emitted from the X-ray tube 11. Specifically, the wedge filter 16 is a filter that allows X-rays emitted from the X-ray tube 11 to pass therethrough and attenuates the X-rays so that the X-rays emitted from the X-ray tube 11 to the subject P exhibit predetermined distribution. For example, the wedge filter 16 (wedge filter or bow-tie filter) is a filter obtained by processing aluminum to have a predetermined target angle and a predetermined thickness.

The collimator 17 is lead plates or the like for narrowing the application range of X-rays that have passed through the wedge filter 16, and includes a slit formed by combining the lead plates or the like.

The DAS 18 reads an energy signal from the X-ray detector 12, and generates digital data (hereinafter also referred to as raw data) indicating a dose value or count value of X-rays detected by the X-ray detector 12 based on the read energy signal. The raw data is a set of a channel number and row number of a source X-ray detection element, a view number indicating a collected view (also referred to as a projection angle), and data indicating the dose value or count value of detected X-rays. The DAS 18 is implemented by, for example, an application specific integrated circuit (ASIC) on which a circuit element capable of generating raw data is mounted. The raw data is transferred to the console 40.

For example, the DAS 18 includes a preamplifier, a variable amplifier, integrating circuitry, and an A/D converter for each detector pixel. The preamplifier amplifies the electrical signal from the connected X-ray detection element with a predetermined gain. The variable amplifier amplifies the electrical signal from the preamplifier with a variable gain. The integrating circuitry integrates electrical signals from the preamplifier for one view period to generate an integral signal. The peak value of the integral signal corresponds to the dose value or count value of X-rays detected by the connected X-ray detection element for one view period. The A/D converter performs A/D conversion on the integral signal from the integrating circuitry to generate raw data.

The bed 30 is a device to place thereon the subject P to be scanned and to move the subject P, and includes a base 31, a bed actuator 32, a table top 33, and a support frame 34.

The base 31 is a case that supports the support frame 34 movably in the vertical direction.

The bed actuator 32 is a motor or actuator that moves the table top 33 on which the subject P is placed in the longitudinal direction of the table top 33. The bed actuator 32 moves the table top 33 in accordance with control by the console 40 or control by the controller 15. For example, the bed actuator 32 moves the table top 33 in the direction orthogonal to the subject P so that the body axis of the subject P placed on the table top 33 matches the central axis of the bore of the rotation frame 13. The bed actuator 32 may also move the table top 33 in the body axis direction of the subject P in accordance with X-ray CT imaging performed using the gantry 10. The bed actuator 32 generates power by driving at a rotation speed corresponding to the duty ratio of the drive signal from the controller 15. The bed actuator 32 is implemented by a motor, such as a direct drive motor or a servo motor.

The table top 33 provided on the top surface of the support frame 34 is a plate on which the subject P is placed. The bed actuator 32 may move not only the table top 33, but also the support frame 34 in the longitudinal direction of the table top 33.

The console 40 includes a memory 41, a display 42, an input interface 43, and processing circuitry 44. Data communication between the memory 41, the display 42, the input interface 43, and the processing circuitry 44 is performed via a bus.

The memory 41 is a storage device, such as a hard disk drive (HDD), a solid state drive (SSD), or an integrated circuit storage device, etc., which stores various types of information. The memory 41 stores, for example, projection data and reconstructed image data. The memory 41 may be not only the HDD, SSD, or the like, but also a driver that writes and read various types of information in and from, for example, a portable storage medium such as a compact disc (CD), a digital versatile disc (DVD), or a flash memory, or a semiconductor memory such as a random access memory (RAM). The storage area of the memory 41 may be in the X-ray CT apparatus 1, or in an external storage device connected via the network. For example, the memory 41 stores data of a CT image or a display image. The memory 41 also stores a control program relating to the present embodiment.

The display 42 displays various types of information. For example, the display 42 outputs a graphical user interface (GUI) or the like for receiving a medical image (CT image) generated by the processing circuitry 44, and various types of operations from the operator. For the display 42, for example, a liquid crystal display (LCD), a cathode ray tube (CRT) display, an organic electro luminescence display (OELD), a plasma display, or any other display can be used as appropriate.

The input interface 43 receives various types of input operations from the operator, converts a received input operation into an electrical signal, and outputs the electrical signal to the processing circuitry 44. For example, the input interface 43 receives, from the operator, an acquisition condition for collecting projection data, a reconstruction condition for reconstructing a CT image, and an image processing condition for generating a post-processing image from the CT image, etc. For the input interface 43, for example, a mouse, a keyboard, a trackball, a switch, a button, a joystick, a touch pad, or a touch panel display can be used as appropriate. In the present embodiment, the input interface 43 does not necessarily include a physical operation component such as a mouse, a keyboard, a trackball, a switch, a button, a joystick, a touch pad, or a touch panel display. For example, the input interface 43 also includes electrical signal processing circuitry that receives an electrical signal corresponding to an input operation from an external input device provided separately from the apparatus, and outputs the electrical signal to the processing circuitry 44.

The processing circuitry 44 controls the overall operation of the X-ray CT apparatus 1 in accordance with the electrical signal of the input operation output from the input interface 43. For example, the processing circuitry 44 includes, as hardware resources, a processor such as a CPU, an MPU, or a graphics processing unit (GPU), and a memory such as a ROM or a RAM. With a processor that executes a program loaded into the memory, the processing circuitry 44 performs a system control function 441, a pre-processing function 442, a reconstruction function 443, an imaging condition setting function 444, an evaluation function 445, and a notification function 446. Each of the functions 441-446 is not necessarily implemented by a single processing circuit. Processing circuitry may be configured by combining a plurality of independent processors, and the processors may execute respective programs to implement the functions 441-446.

The system control function 441 controls each function of the processing circuitry 44 based on an input operation received from the operator via the input interface 43. Specifically, the system control function 441 reads a control program stored in the memory 41, loads it into a memory in the processing circuitry 44, and controls each part of the X-ray CT apparatus 1 in accordance with the loaded control program. For example, the processing circuitry 44 performs each function of the processing circuitry 44 based on an input operation received from the operator via the input interface 43.

The pre-processing function 442 generates data obtained by performing pre-processing, such as logarithmic conversion processing, offset correction processing, processing for sensitivity correction between channels, or beam hardening correction, on detection data output from the DAS 18. The raw data (detection data) before pre-processing and data after pre-processing may be collectively referred to as projection data.

The reconstruction function 443 generates CT image data by performing reconstruction processing using a filtered back projection method (FBP method), a successive approximation reconstruction method, or the like on the projection data generated by the pre-processing function 442.

The imaging condition setting function 444 sets an imaging condition. The imaging condition according to the present embodiment includes parameters such as a tube current, a tube voltage, an acquisition mode, an imaging slice thickness, a thickness and shape of the wedge filter 16, and a rotation speed of the rotation frame 13. The imaging condition setting function 444 also resets the imaging condition based on a changed imaging condition.

The evaluation function 445 evaluates the imaging condition based on information relating to a lower limit range of the X-ray count value that may cause image degradation.

The notification function 446 notifies the operator of the changed imaging condition.

The processing circuitry 44 performs image processing, scan control processing, and display control processing.

The image processing is processing for converting CT image data generated by the reconstruction function 443 into tomographic image data of a given cross section or three-dimensional image data by a publicly-known method, based on the input operation received from the operator via the input interface 43.

The scan control processing is processing for controlling various types of operations relating to X-ray scanning, such as causing the X-ray high voltage device 14 to supply a high voltage to cause the X-ray tube 11 to emit X-rays. For example, the system control function 441 obtains two-dimensional positioning image data of the subject P to determine the scan range, imaging condition, etc. The positioning image data may also be referred to as scanogram data or scout image data.

The display control processing is processing for controlling the display 42 to display information on the middle or result of the processing of each function or process of the processing circuitry 44.

The console 40 is described above as performing a plurality of functions with a single console; however, it is possible to perform a plurality of functions with separate consoles. For example, the functions of the processing circuitry 44, such as the pre-processing function 442 and the reconstruction function 443, may be distributed.

Next, the operation of the X-ray CT apparatus 1 according to the present embodiment will be described with reference to the flowchart of FIG. 2. Described below is an example in which the imaging condition is changed by the tube current (mA) which is one element of the imaging condition.

In step S201, the imaging condition setting function 444 uses positioning image (scanogram or scout image) data obtained in advance to calculate a water-equivalent thickness of the subject from the positioning image by a common calculation method. The positioning image data may be two-dimensional data or three-dimensional data.

In step S202, the imaging condition setting function 444 determines the tube voltage (kV) and acquisition mode used for imaging in accordance with, for example, user's instructions. The acquisition mode enables designation of a read unit (element size) of x-ray detection elements, thereby enabling designation of a high resolution mode to obtain a high resolution image or a super high resolution mode to obtain a super high resolution image.

In step S203, the imaging condition setting function 444 uses an AEC function to determine, based on the water-equivalent thickness, a tube current (mA) used as one parameter of the imaging condition. Hereinafter, the tube current (mA) is referred to as a set mA for convenience. The set mA may be determined based on the water-equivalent thickness and the acquisition mode.

In step S204, the imaging condition setting function 444 determines the gain of the DAS 18 based on the set mA. Specifically, the gain of the DAS 18 is the gain of the variable amplifier included in the DAS 18. The setting function 444 may determine both set mA and gain of the DAS 18 based on the water-equivalent thickness and the acquisition mode. Through step S202 to step S204, an imaging condition is set.

In step S205, the evaluation function 445 refers to a threshold table of low count artifact and determines a lower limit range of the X-ray count value that may cause image deterioration. Here, an mA (referred to as a lower limit mA) corresponding to the maximum value of the count values that may cause a low count artifact is determined. Conceivable conditions that cause the X-ray count value to fall in the lower limit range are, for example, the case where the dose itself is low, and thus the count value is low, and the case where, as the element size is small, the incident X-ray dose is low, and the count value is consequently low.

In step S206, the evaluation function 445 determines whether or not a low count artifact will be produced. Here, the evaluation function 445 compares the set mA determined in step S203 with the lower limit mA determined in step S205, and determines whether or not the set mA is equal to or smaller than the lower limit mA. The operation proceeds to step S207 when the set mA is equal to or smaller than the lower limit mA, and proceeds to step S208 when the set mA is larger than the lower limit mA.

In step S207, the evaluation function 445 changes the imaging condition to prevent the low count artifact from being produced. The notification function 446 notifies the operator of the changed imaging condition. For example, an imaging condition in which at least one parameter of the imaging condition is changed to make the X-ray count value larger than the lower limit range of the count value is calculated. The changed imaging condition may be presented to the operator by being displayed on the display 42. As a specific example of the change of the imaging condition, in the example of this flowchart, the imaging condition setting function 444 may perform setting to increase the tube current so that it is larger than the lower limit mA. As another example of the change of the imaging condition, the imaging condition setting function 444 may perform setting to lower the rotation speed of the gantry (rotation frame 13), setting to increase the imaging slice thickness, or setting to increase the tube voltage (kV). By the system control function 441 controlling the scan based on the setting of the imaging condition, the count value of X-rays that enter one element of the X-ray detector 12 can be increased.

In step S208, the evaluation function 445 determines whether or not the exposed dose of the subject is equal to or larger than a permissible value. The operation proceeds to step S209 when the exposed dose of the subject is equal to or larger than the permissible value, and proceeds to step S210 when the exposed dose of the subject is lower than the permissible value, i.e., within an appropriate range.

In step S209, the notification unit 446 presents to the operator a notice to urge the operator to confirm whether to execute main scan imaging by displaying the notice on the display 42. Even when the X-ray CT apparatus 1 outputs the maximum dose of X-rays, the X-ray count value may be included in the lower limit range, and a low count artifact may not be prevented from being produced. In such a case, it is preferable to present a message to urge confirmation by the operator (e.g., a message to raise attention towards an exposure risk) or the like.

In step S210, main scan imaging is performed. This concludes the operation of the X-ray CT apparatus 1 according to the present embodiment.

An example in which the changed imaging condition is presented to the operator in step S207 is described; however, the operation of step S207 is not limited to this, and imaging may be automatically performed based on the changed imaging condition. Specifically, based on the imaging condition changed by the evaluation function 445, the imaging condition setting function 444 resets the imaging condition so that the changed tube current is supplied. The system control function 441 performs control to perform imaging based on the reset imaging condition.

The evaluation function 445 may determine an element of the imaging condition to be changed based on the priorities of the elements of the imaging condition. For example, in the case of an imaging plan that does not permit a small change in the imaging slice thickness, it is not desirable to increase the imaging slice thickness. Therefore, the evaluation function 445 may change, for example, the tube current of the elements of the imaging condition.

Next, an example of the method for determining the lower limit range of the count value will be described with reference to FIG. 3.

Figures 3, 4:
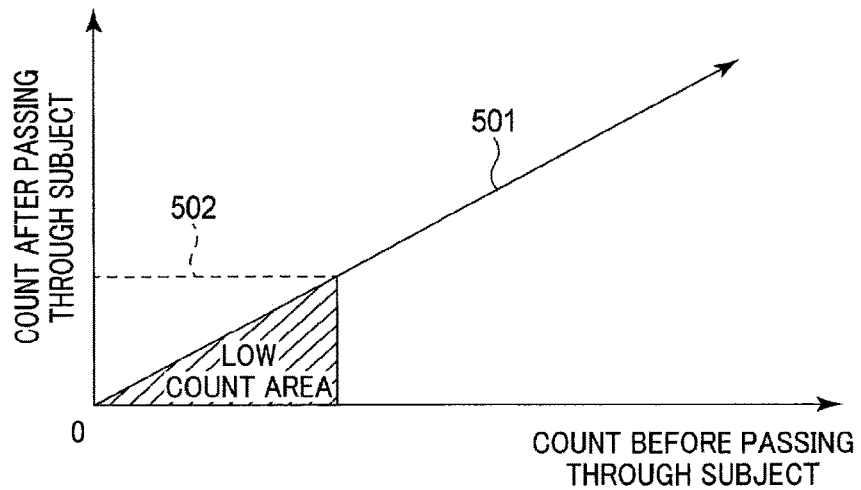
FIG. 3 is a diagram showing an example of a method for determining a tube current according to the present embodiment.
FIG. 4 is a diagram showing an example of a threshold table according to the present embodiment.

FIG. 3 is a graph showing a low count area (lower limit range relating to the count value) based on the body thickness of the subject. The horizontal axis indicates the count value before passing through the subject, and the vertical axis indicates the count value after passing through the subject. Line 501 represents values determined based on the threshold table. The area enclosed by line 501, threshold value 502, and the horizontal axis is the low count area.

The low count artifact is defined by the count amount of X-rays that reach an element of the X-ray detector, and thus can be estimated in advance if the imaging condition and subject body thickness are determined. Therefore, the imaging condition may be changed so that the count value after passing through the subject is not included in the low count area.

Next, an example of the threshold table used for determining line 501 in FIG. 3 will be described with reference to FIG. 4.

The threshold table includes a water-equivalent thickness, radiation quality parameter, acquisition mode, and count value lower limit range. The radiation quality parameter is a parameter relating to radiation quality, and is, for example, the tube voltage (kV) or the type or thickness of the wedge filter.

First, a water-equivalent thickness of the subject is selected. Next, a tube voltage (kV) and a type of the wedge filter, which are radiation quality parameters, are selected. Then, an element size of the X-ray detection element corresponding to the resolution mode of the image, which is the acquisition mode, is selected. The acquisition mode may include body part information of the imaging object. By selecting those elements, the lower limit range of the count value, i.e., threshold 502 in FIG. 3, can be determined. By selecting the water-equivalent thickness, radiation quality parameter, and acquisition mode, line 501 shown in FIG. 3 can also be determined. The threshold table may be further segmentalized using the imaging type and reconstruction condition. The threshold table may be prepared for each view.

The area that causes a low count artifact varies depending on the system, and the hardware of the X-ray CT apparatus 1. Therefore, the threshold table may be updated, for example, when executing a calibration process.

When determining the lower limit mA, the tube current that provides the count value before passing through the subject, which corresponds to the intersection point of threshold 502 and line 501, may be determined.

According to the present embodiment, whether or not the set imaging condition may cause a low count artifact is determined based on the threshold table. When it is determined that a low count artifact may be caused, the imaging condition is changed so as not to cause a low count artifact, and the changed imaging condition is presented to the operator. This makes it possible to present an optimum imaging condition while considering the characteristics of the hardware without causing the operator to be conscious of the setting of the condition to prevent a low count artifact from being produced, and support optimum imaging while reducing unnecessary exposure.

The above-described operation of the X-ray CT apparatus 1 may be realized by an imaging condition management apparatus.

Figure 5:
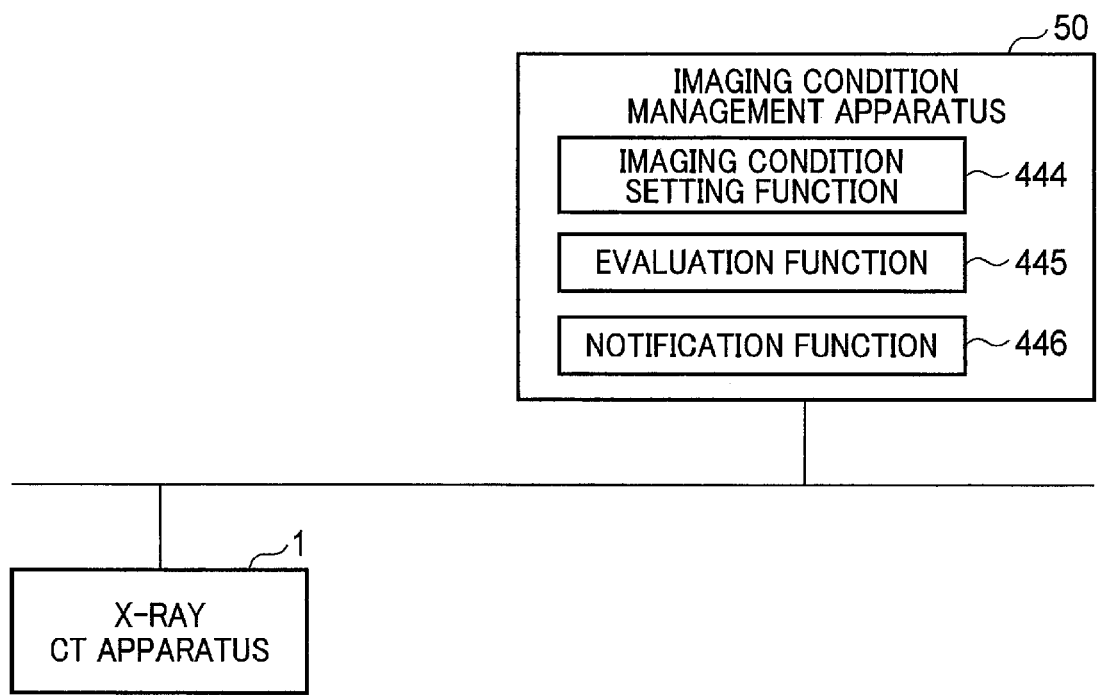
FIG. 5 is a block diagram showing an imaging condition management apparatus according to the present embodiment.

An imaging condition management apparatus to be connected to the X-ray CT apparatus 1 will be described with reference to FIG. 5.

The imaging condition management apparatus 50 includes an imaging condition setting function 444, an evaluation function 445, and a notification function 446. The imaging condition management apparatus 50 is communicably connected to the X-ray CT apparatus 1 by wire or radio.

The imaging condition management apparatus 50 receives a positioning image and an imaging condition (information on the tube voltage, acquisition mode, tube current, and gain) from the processing circuitry 44 of the X-ray CT apparatus 1. The imaging condition management apparatus 50 may receive information on the tube voltage and acquisition mode relating to imaging instead of the imaging condition, and set the tube current and gain to set the imaging condition with the imaging condition setting function 444. Thereafter, as with the above-described processing, the evaluation function 445 determines whether or not a low count artifact is produced, and changes the imaging condition so that the X-ray count value exceeds the lower limit area. The notification function 446 presents the changed condition to the operator.

The X-ray CT apparatus 1 has various types such as a Rotate/Rotate type (third generation CT) in which both the X-ray tube and detector integrally rotate around the subject, and a Stationary/Rotate type (fourth generation CT) in which only the X-ray tube rotates around the subject, which are all applicable to the present embodiment.

The functions of the processing circuitry 44 explained in the embodiment can be executed based on a software program. The functions of the processing circuitry 44 are stored in a magnetic disc (flexible disc, hard disc, etc.), an optical disc (CD–ROM, CD–R, CD–RW, DVD–ROM, DVD±R, DVD±RW, etc.), a semiconductor memory, or a similar storage medium, as a program executable by a computer. As long as a storage medium is readable by a computer or a built-in system, any storage format can be adopted. In this case, the functions of the processing circuitry 44 can be realized by a computer reading the program from the storage medium and executing instructions written in the program on the CPU. In addition, the storage medium is not limited to a medium independent from a computer or a built-in system; a storage medium storing or temporarily storing a program downloaded through LAN (local area network) or the Internet, etc. is also adoptable. Furthermore, the functions of the processing circuitry 44 may be executed not only by means of one storage medium, but also of multiple storage media. In this case, any storage format is adaptable as well.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising:
   an X-ray tube configured to emit first X-rays;
   a detector configured to detect X-rays that have been emitted from the X-ray tube and have passed through a subject; and
   processing circuitry configured to:
   set an imaging condition;
   determine a lower limit range of a count value of the detected X-rays that may cause image degradation by referring to a threshold table of low count artifact, wherein the lower limit range defines an upper boundary of a range of a tube current value where the low count artifact occurs; and evaluate the imaging condition based on information on the lower limit range, wherein the threshold table includes a plurality of thresholds each determined by a water-equivalent thickness, a radiation quality parameter relating to at least one of a tube voltage and a type of wedge filter, and an acquisition mode selected from a plurality of acquisition modes, a read unit of the plurality of acquisition modes being different from each other.

2. The apparatus according to claim 1, wherein the processing circuitry is further configured to, when it is determined that the imaging condition needs to be changed, change the imaging condition so that the count value of the detected X-rays exceeds the lower limit range.

3. The apparatus according to claim 2, wherein the processing circuitry is further configured to change the imaging condition based on priorities of elements of the imaging condition.

4. The apparatus according to claim 2, wherein the processing circuitry is further configured to notify an operator of the changed imaging condition.

5. The apparatus according to claim 1, wherein the processing circuitry is further configured to, when it is determined that the imaging condition needs to be changed, perform at least one of setting to increase a tube current, setting to lower a rotation speed, setting to increase an imaging slice thickness, or setting to increase a tube voltage.

6. The apparatus according to claim 1, wherein the information on the lower limit range is determined in accordance with the subject.

7. The apparatus according to claim 1, wherein the processing circuitry is further configured to notify an operator of a message to urge confirmation by the operator when a count value of a case where a maximum dose of the X-rays is output is included in the lower limit range.

8. The apparatus according to claim 1, wherein the processing circuitry automatically performs imaging based on a changed imaging condition.

9. The apparatus according to claim 1, wherein
the processing circuitry is further configured to change the imaging condition so that the count value of the detected X-rays exceeds the lower limit range when it is determined that the imaging condition needs to be changed, and
imaging is automatically performed based on the changed imaging condition.

10. An imaging condition management apparatus comprising processing circuitry configured to:
set an imaging condition;
determine a lower limit range of a count value of detected X-rays that may cause image degradation by referring to a threshold table of low count artifact, wherein the lower limit range defines an upper boundary of a range of a tube current value where the low count artifact occurs; and
evaluate the imaging condition based on information on the lower limit range, wherein the threshold table includes a plurality of thresholds each determined by a water-equivalent thickness, a radiation quality parameter relating to at least one of a tube voltage and a type of wedge filter, and an acquisition mode selected by a plurality of acquisition modes, a read unit of the plurality of acquisition modes being different from each other.

11. The apparatus according to claim 10, wherein the processing circuitry is further configured to, when it is determined that the imaging condition needs to be changed, change the imaging condition so that the count value of the X-rays exceeds the lower limit range.

12. The apparatus according to claim 11, wherein the processing circuitry is further configured to change the imaging condition based on priorities of elements of the imaging condition.

13. The apparatus according to claim 11, wherein the processing circuitry is further configured to notify an operator of the changed imaging condition.

14. The apparatus according to claim 10, wherein the processing circuitry is further configured to, when it is determined that the imaging condition needs to be changed, perform at least one of setting to increase a tube current, setting to lower a rotation speed, setting to increase an imaging slice thickness, or setting to increase a tube voltage.

15. The apparatus according to claim 10, wherein the information on the lower limit range is determined in accordance with a subject.

16. The apparatus according to claim 10, wherein the processing circuitry is further configured to notify an operator of a message to urge confirmation by the operator when a count value of a case where a maximum dose of X-rays is output is included in the lower limit range.

17. An information processing method for X-ray computed tomography imaging, comprising:
emitting first X-rays;
detecting X-rays that have been emitted from an X-ray tube and have passed through a subject;
setting an imaging condition;
determining a lower limit range of a count value of the detected X-rays that may cause image degradation by referring to a threshold table of low count artifact, wherein the lower limit range defines an upper boundary of a range of a tube current value where the low count artifact occurs; and
evaluating the imaging condition based on information on the lower limit range, wherein the threshold table includes a plurality of thresholds each determined by a water-equivalent thickness, a radiation quality parameter relating to at least one of a tube voltage and a type of wedge filter, and an acquisition mode selected from a plurality of acquisition modes, a read unit of the plurality of acquisition modes being different from each other.

* * * * *